United States Patent
Delli-Santi et al.

(10) Patent No.: US 10,227,478 B2
(45) Date of Patent: Mar. 12, 2019

(54) RESILIENT FOAMS AND USES THEREOF

(71) Applicant: ArthroCare Corporation, Austin, TX (US)

(72) Inventors: George T. Delli-Santi, Scotts Valley, CA (US); Helawe Betre, Round Rock, TX (US)

(73) Assignee: Smith & Nephew, Inc., Memphis, TN (US)

( * ) Notice: Subject to any disclaimer, the term of this patent is extended or adjusted under 35 U.S.C. 154(b) by 218 days.

(21) Appl. No.: 14/734,684

(22) Filed: Jun. 9, 2015

(65) Prior Publication Data

US 2016/0024285 A1    Jan. 28, 2016

Related U.S. Application Data

(60) Provisional application No. 62/028,508, filed on Jul. 24, 2014.

(51) Int. Cl.

| | |
|---|---|
| *A61L 15/28* | (2006.01) |
| *A61L 15/42* | (2006.01) |
| *A61L 31/04* | (2006.01) |
| *A61L 31/14* | (2006.01) |
| *C08L 1/28* | (2006.01) |
| *A61L 27/20* | (2006.01) |
| *A61L 27/52* | (2006.01) |

(Continued)

(52) U.S. Cl.
CPC ............. *C08L 1/286* (2013.01); *A61L 15/28* (2013.01); *A61L 15/425* (2013.01); *A61L 15/60* (2013.01); *A61L 27/20* (2013.01); *A61L 27/52* (2013.01); *A61L 27/56* (2013.01); *A61L 31/042* (2013.01); *A61L 31/145* (2013.01); *A61L 31/146* (2013.01); *C08J 9/28* (2013.01); *C08J 9/40* (2013.01); *A61L 2400/04* (2013.01); *A61L 2400/16* (2013.01); *C08J 2201/0484* (2013.01); *C08J 2205/022* (2013.01); *C08J 2205/06* (2013.01); *C08J 2207/10* (2013.01); *C08J 2301/08* (2013.01)

(58) Field of Classification Search
CPC ......... A61L 15/28; A61L 15/425; C08L 1/286
See application file for complete search history.

(56) References Cited

U.S. PATENT DOCUMENTS

| | | |
|---|---|---|
| 5,718,916 A | 2/1998 | Scherr |
| 6,548,730 B1 * | 4/2003 | Patel ..................... A61L 15/28 602/41 |

(Continued)

FOREIGN PATENT DOCUMENTS

| | | |
|---|---|---|
| EP | 0747420 | 12/1996 |
| EP | 0815879 | 1/1998 |

(Continued)

OTHER PUBLICATIONS

Search Report and Written Opinion for PT-4353-WO-PCT dated Dec. 14, 2015, 14 pages.

(Continued)

*Primary Examiner* — Colin W. Slifka (57) ABSTRACT

Disclosed is a resilient foam and methods of making the foam. The resilient foam includes a derivatized polyanionic polysaccharide and has an open-cell structure. When the resilient foam is contacted with water, the foam forms a thixotropic hydrogel.

23 Claims, 7 Drawing Sheets

(51) Int. Cl.
    *A61L 27/56*     (2006.01)
    *C08J 9/28*     (2006.01)
    *C08J 9/40*     (2006.01)
    *A61L 15/60*     (2006.01)

(56) References Cited

U.S. PATENT DOCUMENTS

| | | |
|---|---|---|
| 2003/0187381 A1 | 10/2003 | Greenawalt et al. |
| 2004/0224021 A1 | 11/2004 | Omidian |
| 2013/0274349 A1* | 10/2013 | Qin .................. C08J 9/0061 |
| | | 514/772.6 |

FOREIGN PATENT DOCUMENTS

| | | |
|---|---|---|
| EP | 2562212 | 2/2013 |
| WO | 2009132225 | 10/2009 |

OTHER PUBLICATIONS

International Preliminary Report on Patentability for related International Patent Application No. PCT/U2015/034902, dated Jan. 24, 2017.

Hoefler, A.C., 2011, "Sodium Carboxymethyl Cellulose: Chemistry, Functionality, and Applications," Food Ingredients Group, Hercules Incorporated, Wilmington, Delaware, www.herc.com/foodgums/index.htm.

EP Examination Report issued Feb. 21, 2018 for corresponding European Patent Application No. 15795000.7-1107; 6 pages.

* cited by examiner

RESILIENT FOAMS AND USES THEREOF

CROSS REFERENCE TO RELATED APPLICATIONS

This application claims benefit to U.S. Provisional Patent Application No. 62/028,508 titled "RESILIENT FOAMS AND USES THEREOF", filed Jul. 24, 2014. The entire contents of the referenced application is incorporated herein by reference.

BACKGROUND OF THE INVENTION

A. Field of the Invention

The invention generally concerns resilient foams, and more specifically to resilient foams made from derivatized polyanionic polysaccharides. The resilient foams are capable of forming a thixotropic hydrogel when contacted with water, blood, wound exudate, etc.

B. Description of Related Art

Medical materials (for example, gels or splints) are intended for use in a variety of surgical procedures (for example, nasal and/or sinus surgery) and/or wound treatments to control bleeding, edema, and prevent adhesions between adjacent soft tissues structures. In recent years there have been numerous efforts to make materials that minimize bleeding and edema that dissolve, biologically degrade, or fragment after performing their function. Examples of some current medical materials are Stammberger Sinu-Foam™ (ArthroCare, Austin, Tex.), NasoPore® (Polyganics, The Netherlands), XeroGel® (Cogent Therapeutics, Haywood, Calif.), SepraGel® (Genzyme, Corp., Cambridge, Mass.), and MeroGel® and MeroPack®, (Medtronic, Jacksonville, Fla.). These materials are foams and/or gels that are malleable, however, they tend not to hold their shape or provide sufficient mechanical force to immobilize soft tissue, for example, nasal structures. Some of these materials must be stored under refrigeration and/or packaged in vacuum packs to inhibit thermal and oxidative degradation of the foam and/or gel. Many of the foamed materials must be hydrated during use to expand the foam, however, many of the materials fail to expand to a size sufficient to fill the cavity and/or provide sufficient mechanical strength to immobilize or support soft tissue. These materials and other current materials are made from polyurethanes and/or cross-linked various derivatives of polyanionic polysaccharides. Bioresorbable gels and stents are also described in U.S. Pat. No. 8,313,762, and U.S. Patent Application Publication No. 2003/0187381.

The problems associated with the current materials are numerous. First, the materials (for example, gels) serve only as a barrier or dressing and cannot be used to separate tissue. Second, many of the materials fragment or remain in the cavity or wound, and must be physically removed during the healing process. Such removal can aggravate the wound. Third, many of the methods to make the materials involve cross-linking processes, which can add several steps and/or expense to the production of the materials. Fourth, many of the materials must be irradiated or further processed to cause chain scission of the cross-linked compounds to promote degradation of the materials.

SUMMARY OF THE INVENTION

A solution to the problems associated with current materials has been discovered. In particular, the solution resides in a resilient foam composed of a derivatized polyanionic polysaccharide and having an open-cell foam structure. The discovery provides several solutions to the problems existing with the current state of the art in this field. For one, cross-linking of the polyanionic polysaccharide with itself, or other polymers, is not required to form a three-dimensional porous foam structure. Second, the resilient foam has the ability to absorb liquids after placement. Third, the resilient foam has robust mechanical properties that allow the resilient foam to spring back when deformed and hold tissue apart, thus eliminating the need for a mechanical splint. Fourth, the resilient foam is flexible and pliable. The ability to be cut to a desired shape and/or size, and/or be bent or folded allows the resilient foam to be inserted into small and/or narrow passages. Fifth, the resilient foam, when contacted with an aqueous composition (e.g., blood, wound exudate, biofluids, water, etc.), forms a thixotropic hydrogel, which can act as a dressing for healing tissues while also maintaining its structure due to its thixotropic properties. After a desired amount of time, the thixotropic hydrogel may be removed by dissolution in water or biofluids. In sum, the resilient foams of the invention are an elegant solution to the problems associated with current medical devices. Other discoveries, in the context of the present invention, are thixotropic hydrogels.

In one aspect of the invention, a resilient foam includes a derivatized polyanionic polysaccharide and has an open-cell foam structure. The polyanionic polysaccharide suitable for the present invention can be any polyanionic polysaccharide known in the art suitable for the production of polysaccharide esters (for example, cellulose). Non-limiting examples of polyanionic polysaccharides include starch and cellulose. Non-limiting examples of derivatized polyanionic polysaccharides include carboxymethyl cellulose, cellulose ethyl sulfonate, carboxymethyl amylose, chondroitin-6-sulfate, chondroitin-4-sulfate, dermatan sulfate, alginate, heparin, heparin sulfate, or any combination thereof. In some embodiments, the derivatized polyanionic polysaccharide is dissolvable. The resilient foam can include 40 wt. % or more of derivatized polyanionic polysaccharide. In some aspects of the invention, the derivatized polyanionic polysaccharide has a degree of substitution of less than 0.6, from 0.2 to 0.55, or from 0.3 to 0.45 derivatives per monomer unit, a non-uniform distribution of the derivatized groups, or any combination thereof. In some instances, the polyanionic polysaccharide has a constant molecular weight per unit length of polyanionic polysaccharide. Without wishing to be bound by theory, it is believed that after derivatization of the polyanionic polysaccharide, the derivatizing groups protrude from the polyanionic polysaccharide backbone. The steric hindrance provided by the protruding derivatizing groups inhibits interactions between the remaining hydroxyl groups. Thus, it is believed that as more hydroxyls are derivatized, the derivatized polyanionic polysaccharide will hydrate more quickly (i.e., be hygroscopic) than a derivatized polyanionic polysaccharide having a lower degree of substitution. For example, carboxymethyl cellulose having a degree of substitution of greater than or equal to 0.7 will be more hygroscopic than carboxymethyl cellulose having a degree of substitution of less than 0.7. (See, for example, Hoefler in *Sodium Carboxymethyl Cellulose*, Hercules Inc., www.scribd.com). It was surprisingly found that while the foams of the invention have a degree of substitution of less than 0.6, they are hygroscopic and able to retain their resiliency after absorbing water in vapor form. For example, the resilient foam can absorb 20 to 60 wt. % of water vapor based on the total weight of the dry foam and remain resilient. Upon absorption of a sufficient amount of additional water in liquid form, the resilient foam forms a thixotropic hydrogel. The derivatized polyanionic polysaccharide and/or resilient foam have not been subjected to cross-linking conditions, thus derivatized polyanionic polysaccharide or foam is not cross-linked or includes a minimal amount of natural or self-cross-linking (for example, two polyanionic polysaccharide molecules crosslinking upon application of heat). For example, the derivatized polyanionic polysaccharide includes 1 wt. % or less of cross-linked polyanionic polysaccharide.

A preferred polyanionic polysaccharide is carboxymethyl cellulose having a degree of substitution of less than 0.6, a non-uniform distribution of the carboxymethyl groups, or any combination thereof. In some aspects of the invention, the resilient foam contains 40 wt. % or more of carboxymethyl cellulose with the balance being water. The carboxymethyl cellulose may have a molecular weight of 50 to 400 kilodaltons from about 100 to about 350, or from 200 to about 400 kilodaltons. In a certain aspect of the invention, the carboxymethyl cellulose is derived from cotton or cotton linters. In some aspects of the invention, the carboxymethyl cellulose is derived from a regenerated cellulose that includes about 200 to about 300 monomer units. In certain aspects of the invention, the carboxymethyl cellulose is derived from rayon, and, more preferably, from viscose rayon fiber. Carboxymethyl cellulose used in the invention can also be derived from cuprammonium rayon, lyocell, saponified rayon, and modulus rayon.

The resilient foam made from the derivatized polyanionic polysaccharide can be porous and can contain up to 60 wt. % of water and remain resilient. In some instances, the resilient foam may include a weight ratio of water to the derivatized polyanionic polysaccharide of about 0.04 to 0.4, from about 0.06 to about 0.3, or about 0.1 to about 0.2. The resilient foam may have 20 to 60 wt. % of water per total weight of resilient foam. Although the resilient foam is hygroscopic, the resilient foam is non-deliquescent. Without wishing to be bound to theory, it is believed that the open-cell structure of the resilient foam allows water in vapor form to fill small pockets in the open-cell foam structure to allow water to be absorbed in less substituted regions of the polyanionic polysaccharide structure. Such a method of absorption allows the resilient foam to be hygroscopic, but retains its resiliency. The resilient foam is also flexible, biodegradable, or both. The resilient foam is a non-liquid, non-flowable foam. In some aspects of the invention the resilient foam is obtained from a thixotropic hydrogel composed of a derivatized polyanionic polysaccharide.

In another aspect of the invention, a thixotropic hydrogel is described. The thixotropic hydrogel is composed of a derivatized polyanionic polysaccharide and water. The polyanionic polysaccharide can have a degree of substitution of less than 0.6, from 0.2 to 0.55, or from 0.30 to 0.45 derivatives per monomer unit, and/or a non-uniform distribution of derivatized groups. The thixotropic hydrogel is composed of 3 to 15 wt. % of the derivatized polyanionic polysaccharide with the balance being water. The thixotropic hydrogel has a yield stress ranging from 200 Pa or more, or from about 200 Pa to about 4000 Pa. Without wishing to be bound by theory, it is believed that the thixotropic hydrogel is a three dimensional structure composed of polysaccharide molecules that are attracted to each other in their less-substituted regions through weak intermolecular attractions and that this attraction provides the thixotropic properties of the hydrogel. The less-substituted regions (hydrophobic regions) are produced by having little to no derivatizing groups in the less-substituted regions of the polyanionic polysaccharide. The less-substituted regions are more difficult to hydrate, and thus it is believed that the slow hydration of the less-substituted regions of the polyanionic polysaccharide allows the thixotropic gel to slowly dissolve in aqueous compositions over time. This ability to slowly dissolve over time allows the thixotropic hydrogel to act as a moist dressing for tissue and to retain its structure due to the thixotropic properties. One of the advantages of the thixotropic property of the gels of the present invention is that they maintain their form or shape and have a decreased tendency to pool or drip.

The resilient foams of the invention can be prepared by (a) obtaining a hydrogel composed of a derivatized polyanionic polysaccharide; (b) subjecting the hydrogel to conditions sufficient to freeze water comprised in the hydrogel; (c) subjecting the hydrogel from step (b) to a drying step sufficient to form an open-cell foam; and (d) contacting the open-cell foam from step (c) with water to form the resilient foam. In some aspects of the invention, steps (b) and (c) may be done at the same time, for example, the hydrogel can be subjected to lyophilization. Lyophilization may include drying at or below the triple point of water, or at 0.10° C. and 4.58 torr. In some instances, the condition step (b) includes subjecting the hydrogel to a temperature of 0° C. to −5° C. for 1 min. to 30 min and then raising the temperature to room temperature over a period of time. In other aspects of the invention, the drying step includes subjecting the hydrogel in step (b) or step (c) to a dehydrating agent, for example, 95 to 100 wt. % ethanol, at a temperature of −5° C. to 25° C. until substantially all water has been absorbed by the ethanol. The open-cell foam obtained in step (c) can be substantially rigid or non-resilient. In step (d) of the invention, the open-cell foam absorbs a sufficient amount of water to form the resilient foam whereby the resilient foam is capable of being deformed upon application of pressure and returning to its original shape after removal of the pressure. In step (d), the foam can absorb 20 to 60 wt. % of water, based on the total weight of the foam. The water in step (d), in some aspects of the invention, is water vapor. The foam may be sterilized prior to step (d) or after step (d). Step (d) may also be combined with step (c) such that drying of the foam is discontinued prematurely (before the foam is fully dried), at a point where remaining water in the foam is sufficient to confer resilience to the open-cell foam.

The resilient foam can be configured for insertion into a cavity or orifice of a subject, and/or to separate opposing tissue surfaces of the subject. The foam can be configured to control bleeding and prevent adhesion between tissue. In some aspects, the foam is configured for insertion into nasal/sinus cavities, an otologic cavity, a cranial cavity, a thoracic cavity, an abdominal cavity, or a pelvic cavity. The resilient foam has sufficient mechanical resilience to separate and hold tissue apart, or to hold tissue away from bone. In some instances, the resilient foam is used as a bandage and/or configured to deliver drugs to a subject. In certain aspects of the invention, the resilient foam of the invention may be administered to treat epistaxis, wounds, or be used in surgical procedures. In some aspects of the invention, the resilient foam and/or thixotropic gel can be administered to a nasal cavity of a subject, and the foam or thixotropic hydrogel may absorb sufficient blood from the subject to stop epistaxis. When treating a wound, the resilient foam can be administered to the wound and the resilient foam absorbs exudate from the wound. When used in surgical procedures, the resilient foam can be inserted in a cavity to separate and hold tissue apart and/or hold tissue away from bone. After coming in contact with biofluids (for example, blood, nasal mucus, or exudate), the resilient foam can form a thixotropic hydrogel, which can act as a moist dressing. Over time, for example from 2 or 3 to 7 days or more, the thixotropic hydrogel dissolves in the biofluids and/or in an aqueous composition provided to the affected area, thereby avoiding the need to surgically remove the foam or hydrogel of the present invention.

Also disclosed in the context of the present invention are embodiments 1 to 112. Embodiment 1 is a resilient foam that includes (a) a derivatized polyanionic polysaccharide; and (b) an open-cell structure, wherein the resilient foam, when contacted with water, is capable of forming a thixotropic hydrogel. Embodiment 2 is the resilient foam of embodiment 1, wherein the derivatized polyanionic polysaccharide has a degree of substitution of less than 0.6 derivatives per monomer unit. Embodiment 3 is the resilient foam of any one of embodiments 1 or 2, wherein the derivatized polyanionic polysaccharide has a degree of substitution from 0.2 to 0.55 derivatives per monomer unit. Embodiment 4 is the resilient foam of embodiment 1, wherein the derivatized polyanionic polysaccharide is a dissolvable polysaccharide. Embodiment 5 is the resilient foam of any one of embodiments 1 to 4, wherein the derivatized polyanionic polysaccharide is carboxymethyl cellulose, cellulose ethyl sulfonate, carboxymethyl amylose, chondroitin-6-sulfate, chondroitin-4-sulfate, dermatan sulfate, alginate, heparin, or heparin sulfate, or any combination thereof. Embodiment 6 is the resilient foam of embodiment 5, wherein the derivatized polyanionic polysaccharide is cellulose ethyl sulfonate. Embodiment 7 is the resilient foam of embodiment 5, wherein the derivatized polyanionic polysaccharide is carboxymethyl cellulose. Embodiment 8 is the resilient foam of embodiment 7, wherein the carboxymethyl cellulose has a non-uniform distribution of carboxymethyl groups. Embodiment 9 is the resilient foam of any one of embodiments 7 or 8, wherein the carboxymethyl cellulose has a consistent weight per unit length of polymer. Embodiment 10 is the resilient foam of any one of embodiments 7 to 9, wherein the carboxymethyl cellulose compound has a molecular weight of 50 to 400 kilodaltons. Embodiment 11 is the resilient foam of any one of embodiments 7 to 10, wherein the carboxymethyl cellulose is derived from cotton or cotton linters. Embodiment 12 is the resilient foam of any one of embodiments 7 to 10, wherein the carboxymethyl cellulose is derived from a regenerated cellulose that includes from about 200 to about 300 monomer units. Embodiment 13 is the resilient foam of any one of embodiments 7 to 10, wherein the carboxymethyl cellulose is derived from rayon. Embodiment 14 is the resilient foam of any one of embodiments 7 to 10, wherein the carboxymethyl cellulose is derived from viscose rayon fiber. Embodiment 15 is the resilient foam of any one of embodiments 7 to 10, wherein the carboxymethyl cellulose is derived from at least one of: cuprammonium rayon, lyocell, saponified rayon, and modulus rayon. Embodiment 16 is the resilient foam of any one of embodiments 1 to 15, further including water, wherein a weight ratio of the water to the derivatized polyanionic polysaccharide ranges from about 0.04 to about 0.6. Embodiment 17 is the resilient foam of any one of embodiments 1 to 14, further including water, wherein an amount of the water ranges from 20 to about 60 wt. % based on the total weight of the resilient foam. Embodiment 18 is the resilient foam of any one of embodiments 1 to 17, wherein the resilient foam comprises 40 wt. % or more of the derivatized polyanionic polysaccharide. Embodiment 19 is the resilient foam of any one of embodiments 1 to 18, wherein the resilient foam is obtained from a hydrogel including the derivatized polyanionic polysaccharide, wherein the hydrogel has a yield stress of 200 Pa or more, or ranging from about 200 Pa to about 4000 Pa. Embodiment 20 is the resilient foam of embodiment 19, wherein the hydrogel includes the derivatized polyanionic polysaccharide in an amount of about 3 to 15 wt. % of the hydrogel. Embodiment 21 is the resilient foam of any one of embodiments 1 to 20, wherein the resilient foam is flexible. Embodiment 22 is the resilient foam of any one of embodiments 1 to 21, wherein the resilient foam is capable of absorbing 60 wt. % or less of water and remain resilient. Embodiment 23 is the resilient foam of any one of embodiments 1 to 22, wherein the resilient foam is a non-liquid, non-flowable foam. Embodiment 24 is the resilient foam of any one of embodiments 1 to 23, wherein the derivatized polyanionic polysaccharide is not cross-linked or comprises a minimal amount of cross-linking Embodiment 25 is the resilient foam of any one of embodiments 1 to 24, wherein the derivatized polyanionic polysaccharide and/or resilient foam has not been subjected to cross-linking conditions. Embodiment 25 is the resilient foam of any one of embodiments 1 to 25, wherein the resilient foam is biodegradable. Embodiment 27 is the resilient foam of any one of embodiments 1 to 26, wherein the resilient foam is porous. Embodiment 28 is the resilient foam of any one of embodiments 1 to 27, wherein the resilient foam is non-deliquescent when exposed to water vapor. Embodiment 29 is the resilient foam of any one of embodiments 1 to 28, wherein the resilient foam is sterile. Embodiment 30 is the resilient foam of any one of embodiments 1 to 29, wherein the resilient foam is configured for insertion into a cavity or orifice of a subject or to separate opposing tissue surfaces of the subject. Embodiment 31 is the resilient foam of embodiment 30, wherein the resilient foam is configured to control bleeding and prevent adhesion to tissue. Embodiment 31 is the resilient foam of any one of embodiments 1 to 30, wherein resilient foam is configured for insertion into nasal/sinus cavities, an otologic cavity, a cranial cavity, a thoracic cavity, an abdominal cavity, or a pelvic cavity. Embodiment 32 is the resilient foam of any one of embodiments 1 to 31, wherein resilient foam is configured for insertion into nasal/sinus cavities, an otologic cavity, a cranial cavity, a thoracic cavity, an abdominal cavity, or a pelvic cavity. Embodiment 33 is the resilient foam of any one of embodiments 1 to 32, wherein the resilient foam is configured for use as a bandage. Embodiment 34 is the resilient foam of any one of embodiments 1 to 33, further including a drug. Embodiment 35 is the resilient foam of any one of embodiments 1 to 34, wherein the thixotropic hydrogel is capable of dissolving in the water. Embodiment 36 is the resilient foam of embodiment 35, wherein some of the thixotropic hydrogel dissolves in the water. Embodiment 37 is the resilient foam of any one of embodiments 35 or 36, wherein the thixotropic hydrogel substantially dissolves in the water.

Embodiment 38 is a resilient foam that includes (a) a derivatized polyanionic polysaccharide having a degree of substitution of less than 0.6 derivatives per monomer unit; and (b) an open-cell structure. Embodiment 39 is the resilient foam of embodiment 38, wherein the degree of substitution ranges from 0.2 to 0.55 derivatives per monomer unit. Embodiment 40 is the resilient foam of embodiments 38 or 39, wherein the derivatized polyanionic polysaccharide is carboxymethyl cellulose, carboxymethyl amylose, chondroitin-6-sulfate, chondroitin-4-sulfate, dermatan sulfate, alginate, heparin, or heparin sulfate, or any combination thereof. Embodiment 41 is the resilient foam of embodiment 40, wherein the derivatized polyanionic polysaccharide is carboxymethyl cellulose. Embodiment 42 is the resilient foam of embodiment 41, wherein the carboxymethyl cellulose has a molecular weight of 50 to 400 kilodaltons. Embodiment 43 is the resilient foam of any one of embodiments 41 to 42, wherein the carboxymethyl cellulose has a substantially consistent molecular weight per unit length. Embodiment 44 is the resilient foam of any one of embodiments 38 to 43, wherein the resilient foam, when contacted with water, is capable of forming a thixotropic hydrogel. Embodiment 45 is the resilient foam of embodiment 44, wherein the thixotropic hydrogel is capable of dissolving in the water. Embodiment 46 is the resilient foam of embodiment 45, wherein a portion of the thixotropic hydrogel dissolves in the water. Embodiment 47 is the resilient foam of any one of embodiments 45 to 46, wherein the thixotropic hydrogel substantially dissolves in the water.

Embodiment 48 is a resilient foam that includes (a) a derivatized polyanionic polysaccharide having a non-uniform distribution of derivatized groups; and (b) an open-cell structure. Embodiment 49 is the resilient foam of embodiment 48, wherein the resilient foam, when contacted with water, is capable of forming a thixotropic hydrogel. Embodiment 50 is the resilient foam of embodiment 49, wherein the thixotropic hydrogel is capable of dissolving in the water. Embodiment 51 is the resilient foam of embodiment 49, wherein some of the thixotropic hydrogel dissolves in the water. Embodiment 52 is the resilient foam of any one of embodiments 50 to 51, wherein the thixotropic hydrogel substantially dissolves in the water. Embodiment 53 is the resilient foam of any one of embodiments 48 to 52, wherein the derivatized polyanionic polysaccharide has a degree of substitution of less than 0.6. Embodiment 54 is the resilient foam of embodiment 53, wherein the degree of substitution ranges from 0.2 to 0.55 derivatives per monomer unit. Embodiment 55 is the resilient foam of any one of embodiments 48 to 54, wherein the derivatized polyanionic polysaccharide is carboxymethyl cellulose, carboxymethyl amylose, chondroitin-6-sulfate, chondroitin-4-sulfate, dermatan sulfate, alginate, heparin, or heparin sulfate, or any combination thereof. Embodiment 56 is the resilient foam of embodiment 55, wherein the derivatized polyanionic polysaccharide is carboxymethyl cellulose. Embodiment 57 is the resilient foam of embodiment 56, wherein the carboxymethyl cellulose has a molecular weight of 50 to 400 kilodaltons. Embodiment 58 is the resilient foam of any one of embodiments 56 to 57, wherein the carboxymethyl cellulose has a substantially consistent molecular weight per unit length.

Embodiment 59 is a thixotropic hydrogel that includes (a) a derivatized polyanionic polysaccharide having a degree of substitution of less than 0.6 carboxymethyl groups per monomer unit; and (b) water, wherein the hydrogel has thixotropic properties. Embodiment 60 is the thixotropic hydrogel of embodiment 59, wherein the degree of substitution ranges from 0.2 to 0.55 derivatives per monomer unit. Embodiment 61 is the thixotropic hydrogel of any one of embodiments 59 to 60, wherein the derivatized polyanionic polysaccharide is carboxymethyl cellulose, carboxymethyl amylose, chondroitin-6-sulfate, chondroitin-4-sulfate, dermatan sulfate, alginate, heparin, or heparin sulfate, or any combination thereof. Embodiment 62 is the thixotropic hydrogel of embodiment 61, wherein the derivatized polyanionic polysaccharide is carboxymethyl cellulose. Embodiment 63 is the thixotropic hydrogel of embodiment 62, wherein the carboxymethyl cellulose has a molecular weight of 200 to 400 kilodaltons. Embodiment 64 is the thixotropic hydrogel of any one of embodiments 62 to 63, wherein the carboxymethyl cellulose has a substantially consistent molecular weight per unit length. Embodiment 65 is the thixotropic hydrogel of any one of embodiments 59 to 64, wherein the derivatives are distributed in the polyanionic polysaccharide in a non-uniform manner. Embodiment 66 is the thixotropic hydrogel of any one of embodiments 59 to 65, wherein the thixotropic hydrogel has yield stress of 200 Pa or more, or ranging from about 200 Pa to about 4000 Pa. Embodiment 67 is the thixotropic hydrogel of embodiment 66, wherein the thixotropic hydrogel comprises the derivatized polyanionic polysaccharide in an amount of 3 to 15 wt. % of the hydrogel. Embodiment 68 is the thixotropic hydrogel of any one of embodiments 58 to 66, wherein the thixotropic hydrogel has a three-dimensional structure, and wherein the water is comprised in the three-dimensional structure.

Embodiment 69 is a thixotropic hydrogel that includes (a) a derivatized polyanionic polysaccharide having a non-uniform distribution of derivatized groups; and (b) water, wherein the hydrogel has thixotropic properties. Embodiment 70 is the thixotropic hydrogel of embodiment 69, wherein the derivatized polyanionic polysaccharide has a degree of substitution of less than 0.6 derivatives per monomer unit. Embodiment 71 is the thixotropic hydrogel of embodiment 70, wherein the degree of substitution ranges from 0.2 to 0.55 derivatives per monomer unit. Embodiment 72 is the thixotropic hydrogel of any one of embodiments 69 to 71, wherein the derivatized polyanionic polysaccharide is carboxymethyl cellulose, carboxymethyl amylose, chondroitin-6-sulfate, chondroitin-4-sulfate, dermatan sulfate, alginate, heparin, or heparin sulfate, or any combination thereof. Embodiment 73 is the thixotropic hydrogel of embodiment 69, wherein the derivatized polyanionic polysaccharide is carboxymethyl cellulose. Embodiment 74 is the thixotropic hydrogel of embodiment 72, wherein the carboxymethyl cellulose has a molecular weight of 200 to 400 kilodaltons. Embodiment 75 is the thixotropic hydrogel of any one of embodiments 73 to 74, wherein the carboxymethyl cellulose has a substantially consistent molecular weight per unit length. Embodiment 76 is the thixotropic hydrogel of any one of embodiments 69 to 75 wherein the derivatives are distributed in the polyanionic polysaccharide in a non-uniform manner. Embodiment 77 is the thixotropic hydrogel any one of embodiments 69 to 76, wherein the thixotropic hydrogel has yield stress of 200 MPa or more, or ranging from about 200 MPa to about 4000 Mpa. Embodiment 78 is the thixotropic hydrogel of embodiment 77, wherein the thixotropic hydrogel comprises the derivatized polyanionic polysaccharide in an amount of 3 to 10 wt. % of the hydrogel. Embodiment 79 is the thixotropic hydrogel of any one of embodiments 69 to 78, wherein the thixotropic hydrogel has a three-dimensional structure, and wherein the water is comprised in the three-dimensional structure. Embodiment 80 is the thixotropic hydrogel of any one of embodiments 69 to 79, wherein the thixotropic hydrogel, when contacted with water, dissolves in the water.

Embodiment 81 is a method of preparing any one of the resilient foams of any one of embodiments 1 to 58, the method including (a) subjecting the hydrogel to conditions sufficient to freeze water comprised in the hydrogel; (b) subjecting the hydrogel from step (b) to a drying step sufficient to form an open-cell foam; and (c) contacting the open-cell foam from step (c) with water to form the resilient foam. Embodiment 82 is the method of embodiment 81, wherein the derivatized polyanionic polysaccharide has a degree of substitution of less than 0.6 derivatives per monomer unit. Embodiment 83 is the method of embodiment 82, wherein the degree of substitution ranges from 0.2 to 0.55 derivatives per monomer unit. Embodiment 84 is the method of any one of embodiment 81 to 82, wherein the derivatized polyanionic polysaccharide has a non-uniform distribution of derivatized groups. Embodiment 85 is the method of any one of embodiments 81 to 84, wherein the derivatized polyanionic polysaccharide is carboxymethyl cellulose, carboxymethyl amylose, chondroitin-6-sulfate, chondroitin-4-sulfate, dermatan sulfate, alginate, heparin, or heparin sulfate, or any combination thereof. Embodiment 86 is the method of embodiment 85, wherein the derivatized polyanionic polysaccharide is carboxymethyl cellulose. Embodiment 87 is the method of embodiment 86, wherein the carboxymethyl cellulose has a molecular weight of 200 to 400 kilodaltons. Embodiment 88 is the method of any one of embodiments 81 to 82, wherein the carboxymethyl cellulose has a substantially consistent molecular weight per unit length. Embodiment 89 is the method of any one of embodiments 86 to 87, wherein the conditions sufficient to freeze water comprised in the hydrogel comprises subjecting the hydrogel to a temperature of 0° C. to −5° C. for 1 min to 30 min. Embodiment 90 is the method of any one of embodiments 81 to 89, wherein the drying step (b) and the freezing step (c) comprises subjecting the hydrogel in step (a) to lyophilization. Embodiment 91 is the method of embodiment 90, wherein lyophilization includes drying at or below the triple, or at 0.1° C. at 4.58 torr. Embodiment 92 is the method of any one of embodiments 81 to 91, wherein the drying step sufficient to form an open-cell foam comprises subjecting the hydrogel in step (b) and/or (c) to 95 to 100 wt. % ethanol at a temperature of −5 to 25° C. until all the water has been absorbed by the ethanol. Embodiment 93 is the method of any one of embodiment 76 to 87, wherein the open-cell foam obtained in step (c) is substantially rigid or non-resilient. Embodiment 94 is the method of any one of embodiments 81 to 93, wherein the open-cell foam in step (d) absorbs a sufficient amount of water to form the resilient foam, wherein the resilient foam is capable of being deformed upon application of pressure and returning to its original shape after removal of the pressure. Embodiment 95 is the method of any one of embodiments 81 to 94, wherein the open-cell foam in step (d) absorbs 20 wt. % to 60 wt. % water. Embodiment 96 is the method of any one of embodiments 81 to 95, wherein the water in step (d) is water vapor. Embodiment 97 is the method of any one of embodiment 76 to 90, further including sterilizing the resilient foam.

Embodiment 98 is a method of forming a thixotropic hydrogel from any one of the resilient foams of embodiments 1 to 58, the method including contacting the resilient foam with an aqueous composition sufficient to form the thixotropic hydrogel. Embodiment 99 is the method of embodiment 98, wherein the aqueous composition is blood. Embodiment 100 is the method of embodiment 99, wherein the aqueous composition is exudate from a wound.

Embodiment 101 is a method for treating epistaxis in a subject, the method including administering any one of the resilient foams of embodiments 1 to 58 to the nasal cavity of a subject, wherein the resilient foam treats the epistaxis. Embodiment 102 is the method of embodiment 101, wherein the resilient foam transforms into a thixotropic hydrogel after coming into contact with blood from the subject.

Embodiment 103 is a method for treating a wound in a subject, the method including administering any one of the resilient foams of embodiments 1 to 58 to the wound of a subject, wherein the resilient foam treats the wound. Embodiment 104 is the method of embodiment 103, wherein the resilient foam transforms into a thixotropic hydrogel after coming into contact with exudate from the wound. Embodiment 105 is the method of embodiment 104, wherein the thixotropic hydrogel dissolves in the exudate from the wound.

Embodiment 106 is a method for treating epistaxis in a subject, the method including administering any one of the thixotropic hydrogels of embodiments 59 to 80 to the nasal cavity of a subject, wherein the thixotropic hydrogel treats the epistaxis. Embodiment 107 is the method of embodiment 106, wherein the thixotropic hydrogel absorbs blood from the subject. Embodiment 108 is the method of any one of embodiments 104 to 107, further including providing sufficient water to the nasal cavity to dissolve the thixotropic hydrogel.

Embodiment 109 is a method for treating a wound in a subject, the method including administering any one of the thixotropic hydrogels of embodiments 59 to 80 to the wound of a subject, wherein the thixotropic hydrogel treats the wound. Embodiment 110 is the method of embodiment 109, wherein the thixotropic hydrogel absorbs exudate from the wound.

Embodiment 111 is a method for absorbing an aqueous composition, the method including contacting the aqueous composition with any one of the resilient foams of embodiments 1 to 58 or any one of the thixotropic hydrogels of embodiment 59 to 80, wherein the aqueous composition is absorbed by the resilient foam or by the thixotropic hydrogel. Embodiment 112 is the method of embodiment, wherein the aqueous composition is blood or exudate.

The following includes definitions of various terms and phrases used throughout this specification.

The term "biodegradable" means capable of being broken down into innocuous products by the action of living things.

The term "degree of substitution" refers to the average number of substituents per monomer unit of polysaccharide. For example, a carboxymethyl cellulose (CMC) having a degree of substitution of 0.2 means that on average the CMC has 2 carboxymethyl groups per 10 anhydroglucose units. The degree of substitution can be determined stoichiometrically based on the polymer weight and the amount of substituents.

The term "degree of polymerization," when referring to polysaccharides and/or polysaccharide esters, shall denote the average number of anhydroglucose monomer units per polysaccharide polymer chain.

The term "epistaxis" means to drip or bleed from the nose (for example, nosebleed).

The term "resilient" refers to an object being able to recoil or spring back into shape after being bent, stretched or compressed.

The term "lyophilizing" means freeze-drying.

The terms "non-uniform distribution of derivatives" or "uniform distribution of derivative" refers to the degree of clustering of the derivatives (substituents) on the backbone of the polysaccharide polymer.

The term "non-cross-linked polysaccharide" means that the polyanionic polysaccharide has not been intentionally subjected to conditions, for example, thermal or chemical conditions, that would promote cross-linking of the polysaccharide with itself and/or other molecules (for example, hyaluronic acid or derivatives thereof). In general, "non-cross-linked polysaccharide" in the context of the present invention includes resilient foams or hydrogels of the present invention having 1 wt. % or less of cross-linked polyanionic polysaccharides.

Figure 5:
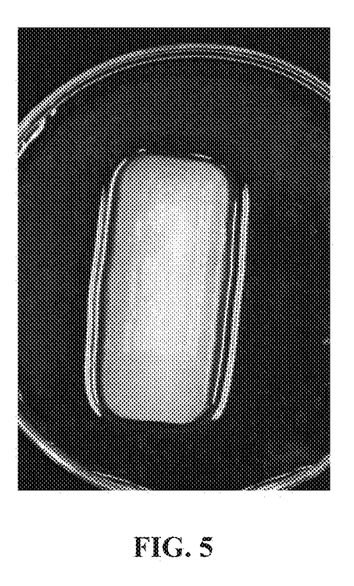
FIG. 5 depicts a photo of an embodiment of the thixotropic hydrogel of the invention formed by addition of water to a resilient foam of the present invention.
Figure 7:
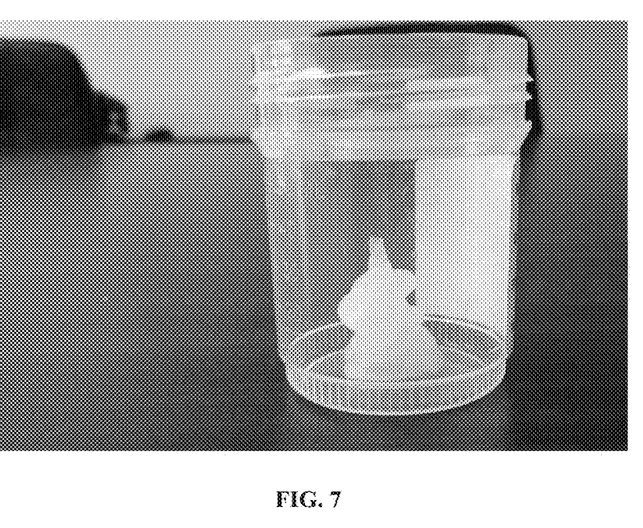
FIG. 7 depicts a photo of a thixotropic gel of the present invention containing carboxymethyl cellulose mixed with water.

The term "thixotropic" refers in the context of this invention is the ability of a gel substance to become flowable when stressed, but return to a non-flowable or fixed form when at rest. For example, the thixotropic hydrogel of the invention may flow under pressure, but return to its non-flowable gel form after pressure is released. FIGS. 5 and 7 provide non-limiting examples of a thixotropic gel of the present invention in a non-flowable or fixed gel form—its shape is maintained until it is subjected to force or pressure.

The term "subject" refers to a human or a mammal.

The term "about" or "approximately" are defined as being close to as understood by one of ordinary skill in the art, and in one non-limiting embodiment the terms are defined to be within 10%, preferably within 5%, more preferably within 1%, and most preferably within 0.5%.

The use of the word "a" or "an" when used in conjunction with the term "comprising" in the claims or the specification may mean "one," but it is also consistent with the meaning of "one or more," "at least one," and "one or more than one."

The words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The methods and catalysts of the present invention can "comprise," "consist essentially of," or "consist of" particular components, compositions, ingredients etc. disclosed throughout the specification. With respect to the transitional phase "consisting essentially of," in one non-limiting aspect, a basic and novel characteristic of the resilient foams, thixotropic hydrogels, and methods of the present invention are their ability to efficiently promote hemostasis, control epistaxis, and/or provide mechanical support.

Other objects, features and advantages of the present invention will become apparent from the following figures, detailed description, and examples. It should be understood, however, that the figures, detailed description, and examples, while indicating specific embodiments of the invention, are given by way of illustration only and are not meant to be limiting. Additionally, it is contemplated that changes and modifications within the spirit and scope of the invention will become apparent to those skilled in the art from this detailed description. In further aspects, features from specific aspects may be combined with features from other aspects. For example, features from one aspect may be combined with features from any of the other aspects.

DETAILED DESCRIPTION OF THE INVENTION

While dissolvable and/or bioresorbable medical materials are known, many of these materials suffer from the deficiencies outlined above. For example, current medical materials may not be resilient, hold their shape, and/or provide sufficient mechanical force to immobilize soft tissue without additional packing Many of the current mechanical materials are provided in a dry state and require hydration of the material prior to use, however, in the hydrated state, the materials provide little to no mechanical strength or resilience, and/or dehydrate during use. For example, many of these materials must be kept moist with sterile saline and/or nasal spray after insertion into a nasal cavity. One potential cause of the mechanical problems is that many of these materials are made through cross-linking of a polyanionic polysaccharide with itself and/or other cross-linking agents. The degree of cross-linking can be difficult to control, and thus cross-linked polymeric structures having inconsistent physical properties may be produced. Such inconsistencies can produce materials having variations in their mechanical properties, which can lead to failure or poor performance of the materials.

The present discovery offers an elegant solution to the inconsistencies and drawbacks of the currently available materials and/or gels by providing a resilient foam that has an open-cell structure and is composed of a polyanionic polysaccharide. The resilient foam, when contacted with water, forms a thixotropic hydrogel. The resilient foam springs back when deformed, provides structural integrity to a tissue, absorb liquids after placement, and/or when contacted with liquids can provide a moist dressing to promote hemostasis.

These and other non-limiting aspects of the present invention are provided in the following sections.

A. Resilient Foam and Thixotropic Hydrogel

Figure 1:
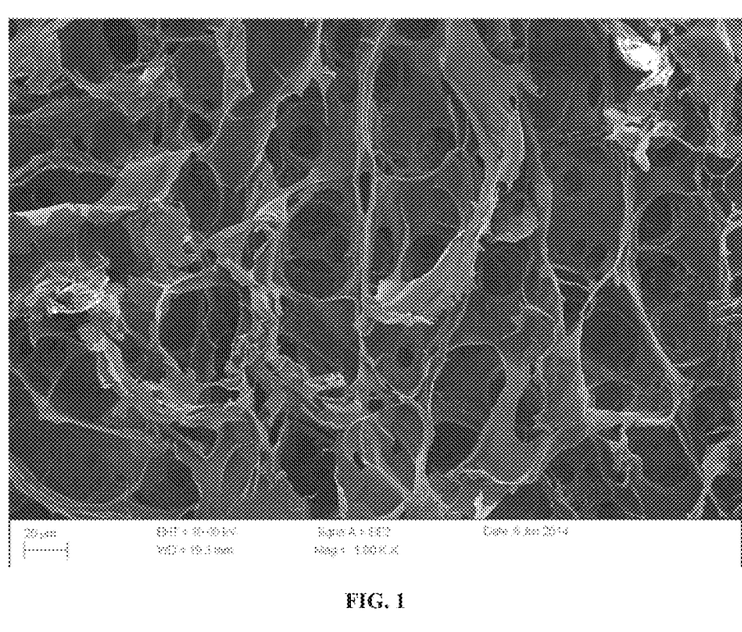
FIG. 1 is a scanning electron micrograph of an embodiment of the resilient foam.
Figure 2:
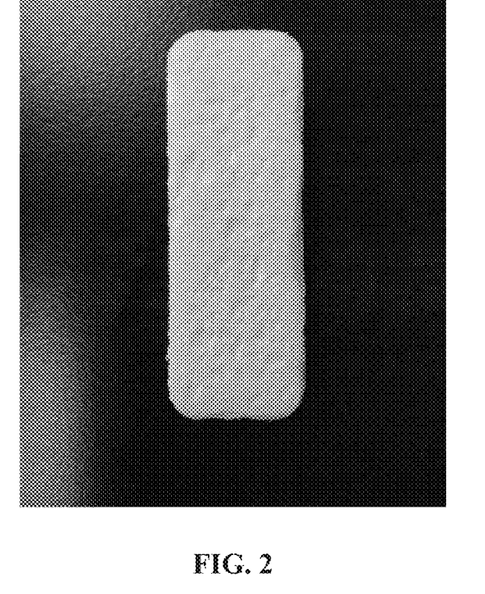
FIG. 2 is a photo of a cross-sectional portion of an embodiment of the resilient foam.
Figure 3:
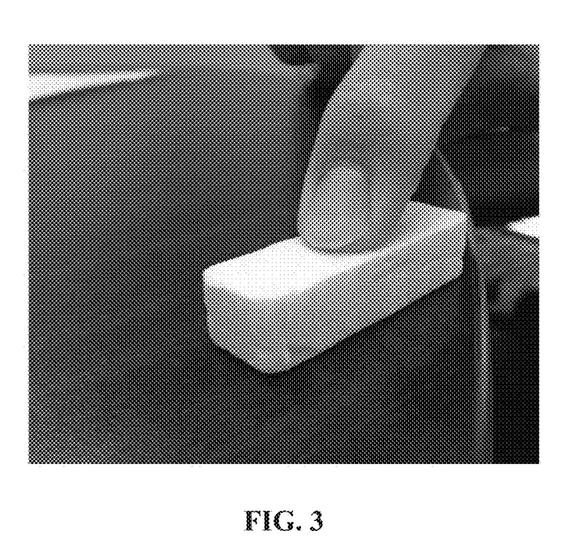
FIG. 3 is a photo of an embodiment of the rigid open-cell foam prior to treatment with water (i.e., a non-resilient foam).
Figure 4A:
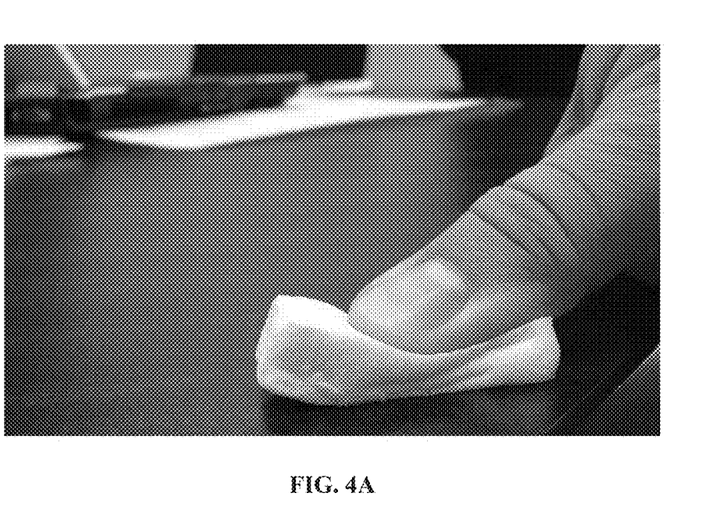
FIG. 4A is a photo of an embodiment of a resilient foam of the present invention with pressure being applied.
Figure 4B:
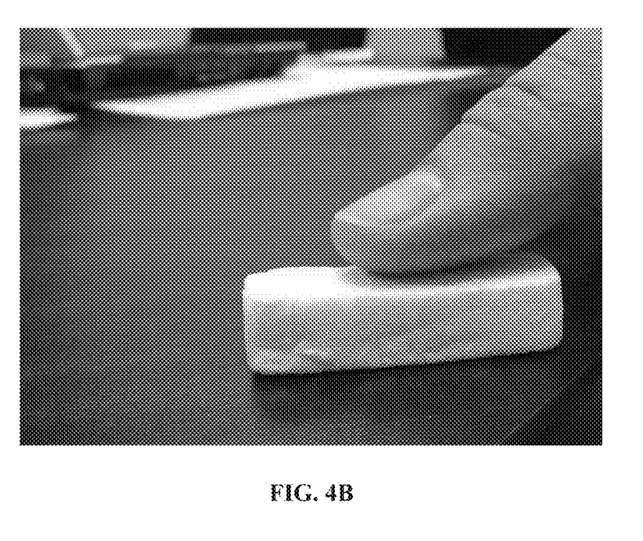
FIG. 4B is a photo of the resilient foam in FIG. 4A after release of pressure.

FIG. 1 is a scanning electron micrograph of an embodiment of the resilient foam made from carboxymethyl cellulose. As shown in FIG. 1, the resilient foam has a three-dimensional structure with interconnected openings throughout the carboxymethyl cellulose foam structure. Thus, the resilient foam has a three-dimensional open-cell structure. FIG. 2 is a photo of a cross-sectional piece of the resilient foam. As shown, in FIG. 2, the foam has a sponge-like structure. FIG. 3 is a photo of an embodiment of the rigid open-cell foam prior to treatment with water. As shown in FIG. 3, application of force to the foam (e.g., the finger is pressing on the foam) does not deform the foam. Thus, the open-cell foam is rigid and has little to no resilience prior to treatment with water. FIGS. 4A and 4B are photos of an embodiment of the rigid foam (for example, the foam in FIG. 3) after treatment with water to produce a resilient foam of the present invention. As shown in FIG. 4A, application of force to the surface of the resilient foam (e.g., pushing down on the surface with a finger) moves the surface of the foam in the direction of the applied force (e.g., downward). When the applied force is removed (e.g., the finger is lifted), the surface of the foam returns to its substantially original state as shown in FIG. 4B. Thus, the resilient foam is capable of being stressed and upon release of the stress returns to its original, or substantially original, shape. Further, the resilient foam is pliable and flexible. For example, the two sides of the resilient foam can be folded towards each other without breaking or tearing of the foam surface. The resilient foam can also be squeezed, and/or cut to a required size. Such mechanical properties allow the resilient foam to contour to a body cavity or wound as required, separate and hold tissue apart, separate tissue and hold tissue away from bone, provide mechanical and/or chemical hemostasis, control epistaxis, prevent adhesion, minimize bleeding, swelling and edema, or any combination thereof. Upon contact with an aqueous composition (for example, water, saline, or biofluids), the foam becomes a thixotropic hydrogel. FIG. 5 depicts a photo of an embodiment of the thixotropic hydrogel of the invention formed by addition of water to the foam. The thixotropic hydrogel and/or foam may remain in place for a period of time, for example 2 days, 3 days, 7 days, 10 days or longer, or until removed by dissolution with a water solution or dissolution in biofluids. The thixotropic hydrogel and foam slowly dissolve in aqueous compositions over time. The rate of dissolution of the thixotropic hydrogel and/or foam in water can be controlled by the amount of aqueous composition provided to the foam and/or thixotropic hydrogel. Without wishing to be bound by theory, it is believed that exposure to an excess amount of water (for example, absorption of greater than 60 wt. % of water) will cause the foam to develop into a hydrogel and further develop a concentration gradient as water diffuses into the hydrogel (i.e., high water and low polyanionic polysaccharide content at the polyanionic polysaccharide gel and water interface that then increases to a high polyanionic polysaccharide and low water content, thixotropic gel within the center of the hydrogel bolus). Water will continue to diffuse into the hydrogel bolus due to the presence of an osmotic gradient across the water and low polyanionic polysaccharide interface. When the polyanionic polysaccharide concentration reaches about 3 wt. % (i.e., the weight percent of the polysaccharide continues to decrease as the foam or gel absorbs more water), the hydrogel will lose its thixotropic property and become a viscous aqueous polyanionic polysaccharide solution. This viscous aqueous solution will then continue to become more dilute as more water diffuses into the hydrogel bolus. In this manner, the thixotropic polyanionic polysaccharide gel bolus undergoes dissolution from the interface between the gel bolus and water interface inward. The rheology of the gel bolus will vary from fully thixotropic at its center to a non-thixotropic viscous polyanionic polysaccharide solution at the periphery of the bolus. In between these extremes, will be a swollen thixotropic hydrogel and a moving conversion zone wherein thixotropy breaks down when the polyanionic polysaccharide concentration is 3 wt. % or less.

B. Derivatized Polyanionic Polysaccharides

Derivatized polyanionic polysaccharides (for example, esters) can be formed by the reaction of a polysaccharide with a derivatizing compound. Examples of derivatizing compounds include haloacids, alkyl halides, and alkyl oxides, etc. A non-limiting example of a derivatized polyanionic polysaccharide is carboxymethyl cellulose. In one aspect of the invention, the polyanionic polysaccharide can be obtained having a specified amount of repeating units (for example, 200-300 repeating units). The polyanionic polysaccharide can have a molecular weight ranging from about 50 to about 400, or from about 100 to about 300 kilodaltons.

The polysaccharide can be a β-1,4-linked polymer having a plurality of anhydroglucose monomer units. The polysaccharide suitable for use in the present invention can generally have the following structure:

(I)

where n is the degree of polymerization.

The polysaccharide can have a uniform molecular weight per unit length of polymer. Additionally, the polysaccharide suitable for use in the present invention can be in the form of a sheet or fiber. In a preferred aspect, the polysaccharide is in the form of a viscose rayon fiber.

Derivatized polyanionic polysaccharides (for example, derivatized cellulose) can be prepared by contacting a polyanionic polysaccharide with base in the presence of an acylating agent using methods known in the art. (See, for example, U.S. Pat. No. 4,410,694). A non-limiting example of the general reaction for derivatization of polyanionic polysaccharide is as follows:

(1)

(2)

where R is polyanionic polysaccharide having structure (I)

Contact of the acylating reagent (for example, chloroacetic acid) with the polyanionic polysaccharide at a contact temperature and contact time is sufficient to provide the derivatized polyanionic polysaccharide (for example, carboxymethyl cellulose) with a desired degree of substitution. The amount of derivatization can be determined stoichiometrically from the average molecular weight of the polyanionic polysaccharide, knowledge of number of anionic groups, and knowledge of the amount of acylating agent. The resulting derivatized polyanionic polysaccharide used to prepare the resilient foam of the invention has a degree of substitution that is less that about 0.6, from 0.2 to 0.55, or from 0.3 to 0.45. In some embodiments, the derivatized polyanionic polysaccharide is a dissolvable polysaccharide, for example, a sugar. Such a derivatized polyanionic polysaccharide may not be dependent on the degree of substitution of dissolution to occur. A non-limiting example to prepare derivatized cellulose includes continuously circulating a homogeneous alkaline liquid through viscose rayon fibers in a reaction vessel. The homogeneous alkaline liquid includes an effective amount of an esterifying agent and salts thereof (for example, chloroacetic acid and sodium choroacetic acid), a homogeneous alkaline reactant (for example, sodium hydroxide), alcohol (for example, ethanol) and water. Circulating the homogeneous alkaline liquid through the viscose rayon fibers at a temperature, for example, 60 to 70° C., for a sufficient time converts the rayon fibers into carboxymethyl cellulose fibers. The carboxymethyl cellulose fibers can be washed and the alcohol removed under partial vacuum to produce substantially pure carboxymethyl cellulose fibers. In one aspect of the invention, the carboxymethyl cellulose fibers can be physically processed (for example, knitted) for ease of handling. Similar processes can be performed to derivatize polysaccharides to produce carboxymethyl amylose, chondroitin-6-sulfate, chondroitin-4-sulfate, dermatan sulfate, alginate, heparin, or heparin sulfate, or any combination thereof.

Figure 6A:
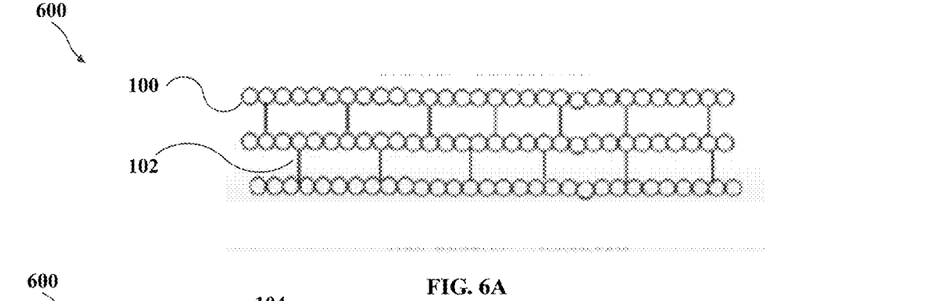
FIG. 6A depicts a schematic of uniform distribution of derivatizing groups in derivatized cellulose.
Figure 6B:
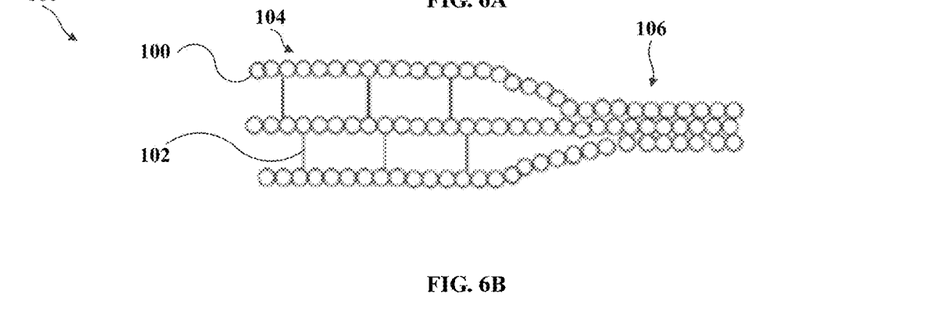
FIG. 6B depicts a schematic of non-uniform distribution of derivatizing groups in cellulose.

Derivatization of the polyanionic polysaccharide can result in a non-uniform distribution of the derivatized groups. Without wishing to be bound by theory, it is believed that when a non-uniformly substituted derivatized polyanionic polysaccharide is blended with another fluid, the resulting fluid will have non-uniform properties, non-Newtonian flow properties, and/or thixotropic properties. FIGS. 6A and 6B are schematics depicting uniform and non-uniform structures of carboxymethyl cellulose. In FIG. 6A, cellulose 600 includes layers of cellulose molecules 100 and carboxymethyl groups 102. As shown, the layers of cellulose molecules 100 are separated by uniformly distributed carboxymethyl groups 102 in the cellulose. This uniform distribution of carboxymethyl groups allows fluid (for example, water) to flow between the layers of cellulose molecules which hydrates the cellulose. Hydrating the cellulose decreases the hydrogen bonding between cellulose layers and promotes dissolution of the cellulose into the fluid. Said another way, carboxymethyl cellulose with uniformly distributed carboxymethyl groups will easily dissolve in water. As shown in FIG. 6B, the layers of cellulose molecules 100 in portion 104 are separated by uniformly distributed carboxymethyl groups 102 while the layers of cellulose molecules in portion 106 are not separated and/or do not contain the carboxymethyl groups. Without wishing to be bound by theory, it is believed that the non-derivatized portion of the cellulose is bound together through intermolecular interaction, thus this portion of the cellulose is not as susceptible to hydration. Therefore, this portion of the carboxymethyl cellulose is insoluble or partially insoluble in water. Since the derivatized portion of the cellulose is more susceptible to hydration, this portion of the carboxymethyl cellulose may be partially soluble or soluble in water. Due to the insolubility of the non-derivatized portions of the carboxymethyl cellulose and the solubility properties of the derivatized portions of carboxymethyl cellulose, the carboxymethyl cellulose when treated with sufficient fluid (for example, 60 wt. % or more of water or biofluids) form a gel having non-uniform, non-Newtonian flow properties, and thixotropic properties.

C. Preparation of Resilient Foams and Thixotropic Hydrogels

The derivatized polyanionic polysaccharide (for example, the carboxymethyl cellulose fibers) described in Section B above, can be dissolved in water to produce a gel having from about 3 to 15 wt. %, 4 to 9 wt. %, or 5 to 8 wt. % of derivatized polyanionic polysaccharide with the balance being water. Any type of water (for example, deionized, filtered, or potable) may be mixed with the polyanionic polysaccharide. A non-limiting example, of a gel of the invention is a carboxymethyl cellulose hydrogel. In some aspects of the present invention the produced gel is a thixotropic hydrogel. FIG. 7 depicts a photo of a thixotropic gel formed by adding water to carboxymethyl cellulose of the present invention. The gel and/or thixotropic hydrogel may be stored, packaged for sale, sterilized, or further processed into a resilient foam of the invention.

The resilient foam of the invention can be made from the previously described derivatized polyanionic polysaccharide gel and/or the polyanionic polysaccharide thixotropic hydrogel by subjecting them to freezing, drying, and hydrating treatments. In a non-limiting example, the gel composed of carboxymethyl cellulose and water may be placed in a mold of a chosen shape and size (for example, a contoured mold shaped to resemble a nasal cavity). The mold may be subject to temperatures that are less than the freezing temperature of water, for example, less than 0° C. After 0° C. is reached, the temperature can be reduced further over time. For example, the temperature is reduced by a few degrees then maintained at the lower temperature for a period of time, and then reduced again until the lowest desired temperature is reached, for example, a temperature from 0° C. to −5° C., where the sample is held for a period of time (for example, 1 minute to 30 minutes). The frozen gel may be subjected to a drying step to produce the dry rigid foam. The dry rigid foam is composed of about 90 wt. % or more of derivatized polyanionic polysaccharide with the balance being water. In one aspect of the invention, the frozen gel is subjected to drying under vacuum at a temperature of 0° C. For example, the frozen gel can be placed under a vacuum of 0.005 ton to about 0.2 ton at −40° C. and the temperature is raised over a period of time to room temperature. In some aspects of the invention, the freezing and drying may be performed as one process, for example, as a lyophilization process. Without wishing to be bound by theory, it is believed that freezing the thixotropic hydrogel transforms water in the hydrogel to ice and the ice sublimates from the gel when dried under reduced pressure and temperatures below 0° C. Sublimation of the ice preserves and/or opens the three dimensional structure of the gel into a dry rigid foam structure having an open-cell structure. In another aspect of the invention, the dried and/or frozen gel is treated with 95 to 100 wt. % ethanol at a temperature of −5° C. to 25° C., or from −5° C. to 15° C. until substantially all of the water is removed from the frozen and/or dried foam.

The resulting dry rigid porous foam can be made resilient by exposing the dry rigid foam to water (for example, water vapor) for at least 30 hours. Exposing the dry rigid foam to water vapor allows the water to be slowly absorbed through the bulk of the foam, which provides uniform resilience throughout the foam. As a non-limiting example, the foam can be exposed to air at a relative humidity of about 40 to 100%, or from 50 to 80% for about 30 to 48 hours. The resilient foam may absorb up to 60 wt. %, or from 20 to 60 wt. %, 25 to 50 wt. %, or 30 to 40 wt. % of water with the balance being derivatized polyanionic polysaccharide. For example, the resilient foam may be composed of 80 wt. % of derivatized polyanionic polysaccharide and 20 wt. % water, 75 wt. % derivatized polyanionic polysaccharide and 25 wt. % water, or 60 wt. % derivatized polyanionic polysaccharide and 40 wt. % water. The resilient foam may be sterilized before or after exposing the foam to water. For example, the dry rigid foam may be sterilized under ethylene oxide conditions prior to exposing the foam to water vapor to make it resilient.

The resilient foam can be contacted with an aqueous composition (for example, water, blood, saline, nasal mucus, and wound exudate) to form a thixotropic hydrogel. For example, the resilient foam can be treated contacted water over a period of time, for example, 2, 3, or 10 day. Without wishing to be bound by theory, it is believed that the water penetrates the cellulose structure via the open-cell causing the foam to lose its rigidity and form a thixotropic hydrogel. A rate of thixotropic hydrogel formation can be varied, for example, by altering the amount of fluid (for example, saline) contacted with the resilient foam. The thixotropic hydrogel may be applied to a wound or tissue as a packing or a moist dressing.

D. Use of the Resilient Foam

The resilient foam may be used in surgical procedures, treatment of epistaxis, treatment of wounds, or any combination thereof. In general, the time period required for effective treatment can vary according to the type of surgery, bleeding, the type of tissues involved, and/or injury involved. The resilient foam can contour to the body cavity or wound as required, and provide mechanical/chemical hemostasis, control epistaxis, provide mechanical resilience, prevent adhesion, and minimize swelling and edema. Generally, if the resilient foam is used to separate tissue, the tissues should remain separated for at least 48 hours, and preferably, for a period of at least 2 to 7 days. As the resilient foam is contacted with an aqueous composition (for example, blood, saline, nasal mucus, and wound exudate), it will form a thixotropic hydrogel. A rate of thixotropic hydrogel formation can be varied, for example, by altering the amount of fluid (for example, saline) contacted with the resilient foam. The resilient foam compositions of the invention can be especially useful in preventing adhesion between tissues following nasal and sinus surgery and in the treatment of epistaxis. The resilient foam compositions of the invention can also be used for other types of surgery or wound treatment. Depending on the particular surgery or wound treatment for which the resilient foam composition is used for, the resilient foam composition may be provided in any desired size and shape suitable to optimize its use.

Resilient foams of the present invention can further be used for drug delivery. For example, resilient foam compositions containing water-insoluble or partially water soluble polyanionic polysaccharides can be useful for sustained release drug delivery. The drug to be delivered can be dispersed within the composition, or can be covalently bonded to the resilient foam; and the resilient foam can then be implanted at the locus where delivery is desired. In some aspects of the invention, the thixotropic hydrogel may be applied to a nasal cavity to control epistaxis, bleeding, and/or provide a moist dressing.

EXAMPLES

The present invention will be described in greater detail by way of specific examples. The following examples are offered for illustrative purposes only, and are not intended to limit the invention in any manner. Those of skill in the art will readily recognize a variety of noncritical parameters which can be changed or modified to yield essentially the same results.

Example 1

Preparation of a Resilient Foam and Thixotropic Hydrogel

Figure 8:
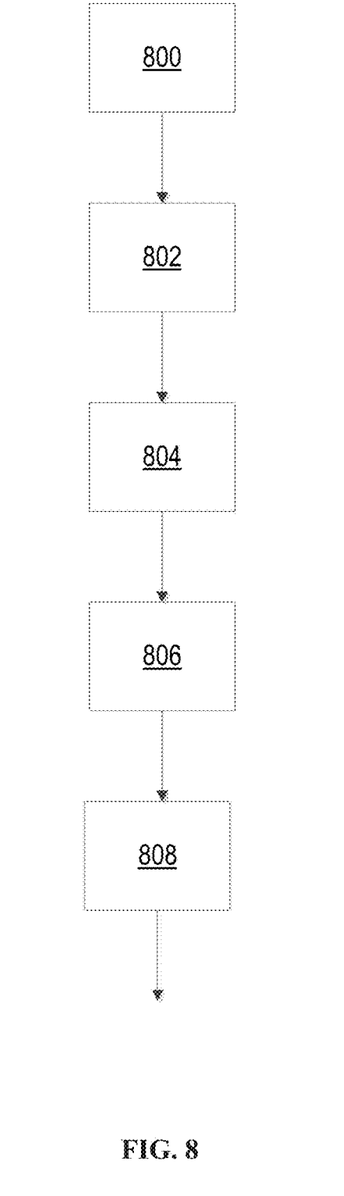
FIG. 8 depicts a flow chart of a process to make the resilient foam of the present invention.

The resilient foam can be prepared as outlined in the flow chart of shown in FIG. 8. In step 800, rayon was converted to carboxymethyl cellulose knit. The carboxymethyl cellulose knit was dissolved in water to form a gel having about 7 wt. % of carboxymethyl cellulose with the balance being water (Step 802). The gel was cast into a mold shaped and sized for use as a nasal stent (Step 804). The mold was subject to freeze drying conditions (Step 806) to form the rigid foam as depicted in FIG. 3. The rigid foam in Step 806 was subjected to water vapor to form the resilient foam (Step 808) depicted in FIGS. 4A and 4B.

The invention claimed is:

1. A resilient foam comprising:
   (a) a derivatized polyanionic polysaccharide; and
   (b) an open-cell structure, wherein
      (i) the resilient foam, when contacted with water, is capable of forming a thixotropic hydrogel, and
      (ii) the derivatized polyanionic polysaccharide has a degree of substitution of less than 0.6 derivatives per monomer unit.

2. The resilient foam of claim 1, wherein the derivatized polyanionic polysaccharide is dissolvable in water.

3. The resilient foam of claim 1, wherein the derivatized pdyamomc polysaccharide is carboxymethyl cellulose, cellulose ethyl sulfonate, carboxymethyl amylose, chondroitin-6-sulfate, chondroitin-4-sulfate, demiatan sulfate, alginate, heparin, or heparin sulfate, or any combination thereof.

4. The resilient foam of claim 3, wherein the derivatized polyanionic polysaccharide is carboxymethyl cellulose.

5. The resilient foam of claim 4, wherein the carboxymethyl cellulose has a non-uniform distribution of carboxymethvl groups.

6. The resilient foam of claim 4, wherein the carboxymethyl cellulose has a consistent weight per unit length of polymer.

7. The resilient foam of claim 4, wherein the carboxymethyl cellulose compound has a molecular weight of 50 to 400 kilodaltons.

8. The resilient foam of claim 4, wherein the carboxymethyl cellulose is derived from cotton or cotton linters.

9. The resilient foam of claim 1, wherein the derivatized polyanionic polysaccharide is cellulose ethyl sulfonate.

10. The resilient foam of claim 1, further comprising water, wherein a weight ratio of the water to the derivatized polyanionic polysaccharide ranges from about 0.04 to about 0.6.

11. The resilient foam of claim 1, further comprising water, wherein an amount of the water ranges from 20 to about 60 wt. % based on the total weight of the resilient foam.

12. The resilient foam of claim 1. Wherein the resilient foam comprises 40 wt. % or more of the derivatized polyanionic polysaccharide.

13. The resilient foam of claim 1, wherein the resilient foam is obtained from a hydrogel comprising the derivatized polyanionic polysaccharide, wherein the hydrogel has a yield stress of 200 Pa or more.

14. The resilient foam of elhim 13, wherein the hydrogel comprises the derivatized polyanionic polysaccharide in an amount of about 3 to 15 wt. % of the hydrogel.

15. The resilient foam of claim 1, wherein the resilient foam is flexible.

16. The resilient foam of claim 1, wherein the resilient foam is capable of absorbing 60 wt. % of less of water and remain resilient.

17. The resilient foam of claim 1, wherein the resilient foam is a nonliquid, non-flowable foam.

18. The resilient foam of claim 1, wherein the derivatized polyanionic polysaccharide 1% or less of cross-linked polyanionic polysaccharide.

19. The resilient foam of claim 1, wherein the derivatized polyanionic polysaccharide and/or resilient foam has not been subjected to cross-linking conditions.

20. The resilient foam of claim 1, wherein the resilient foam is non-deliquescent when exposed to water vapor.

21. The resilient foam of claim 1, the degree of substitution is between 0.2 to 0.55 derivatives per monomer unit.

22. The resilient foam of claim 21, the degree of substitution is between 0.3 to 0.45 derivatives per monomer unit.

23. The resilient foam of claim 1, wherein the resilient foam is hygroscopic and the resilient foam is capable of retaining resiliency after absorbing water in vapor form.

\* \* \* \* \*